US011185602B1

United States Patent
Leal-Quiroz et al.

(10) Patent No.: US 11,185,602 B1
(45) Date of Patent: Nov. 30, 2021

(54) DECONTAMINATION OF BODY SURFACES AND ARTICLES WITH HARMLESS RADIATION AND RELATED METHODS

(71) Applicants: Edbertho Leal-Quiroz, Fresno, CA (US); Isabel Leal, Fresno, CA (US); David A. Leal, Fresno, CA (US)

(72) Inventors: Edbertho Leal-Quiroz, Fresno, CA (US); Isabel Leal, Fresno, CA (US); David A. Leal, Fresno, CA (US)

( * ) Notice: Subject to any disclaimer, the term of this patent is extended or adjusted under 35 U.S.C. 154(b) by 0 days.

(21) Appl. No.: 17/336,137

(22) Filed: Jun. 1, 2021

Related U.S. Application Data

(60) Provisional application No. 63/032,472, filed on May 29, 2020.

(51) Int. Cl.
*A61L 2/00* (2006.01)
*A61H 21/00* (2006.01)

(52) U.S. Cl.
CPC .......... *A61L 2/0047* (2013.01); *A61L 2/0058* (2013.01); *A61L 2202/11* (2013.01); *A61L 2202/122* (2013.01); *A61L 2202/14* (2013.01)

(58) Field of Classification Search
CPC ...... A61N 5/00; A61N 5/0624; A61N 5/0616; A61L 2/0047; A61L 2/0058; A61L 2/085; A61L 2202/20

(Continued)

(56) References Cited

U.S. PATENT DOCUMENTS 5,714,119 A  2/1998 Kawagoe et al.
5,920,075 A  7/1999 Whitehead
(Continued)

FOREIGN PATENT DOCUMENTS

CA  2399851  4/2003
CN  105377312  3/2016
(Continued)

OTHER PUBLICATIONS

English translation of RU2663459 abstract retrieved on Jun. 4, 2021 from "https://worldwide.espacenet.com/patent/search/family/054249628/publication/RU2663459C1?q=pn%3DRU2663459C1".

(Continued)

*Primary Examiner* — Monzer R Chorbaji
(74) *Attorney, Agent, or Firm* — Sierra IP Law, PC; William K. Nelson

(57) ABSTRACT

A system and method that include using biophotonic and/or phononic systems for deactivating viruses, bacteria, and other pathogens that may be present on people, their clothing, or other surfaces. Biophotonic refers to the use of photons in specific wavelengths of the FAR-Ultraviolet C radiation and/or FAR-Infrared C radiation to affect the interior structure and chemistry of bacteria and viruses to degrade them and render them harmless. The infrared radiation may also provide a phononic effect that degrades the physical conditions of the cell or virus sufficiently to disrupt the cellular machinery, deactivating the virus. Furthermore, a higher temperature Inside the UVIR system makes negligible the rate of propagation of the Virus. The system of the present invention is operable to use electromagnetic radiation to disinfect the exterior surfaces of living mammal animals without harming the animal's tissue, but still effective to degrade microbe and sanitize the exterior surfaces.

19 Claims, 6 Drawing Sheets

(58) Field of Classification Search
USPC .................................. 422/22, 24; 607/86
See application file for complete search history.

(56) References Cited

U.S. PATENT DOCUMENTS

| | | | |
|---|---|---|---|
| 6,656,424 | B1 | 12/2003 | Deal |
| 6,911,177 | B2 | 7/2005 | Deal |
| 6,960,201 | B2 | 11/2005 | Cumbie |
| 7,328,708 | B2 | 2/2008 | Malak |
| 7,424,314 | B2 | 9/2008 | Park |
| 8,067,750 | B2 | 11/2011 | Deal |
| 8,277,741 | B2 | 10/2012 | McCabe |
| 8,481,985 | B2 | 7/2013 | Neister |
| 8,617,479 | B2 | 12/2013 | Gil et al. |
| 8,624,202 | B2 | 1/2014 | Gil |
| 8,696,985 | B2 | 4/2014 | Gil et al. |
| 8,791,441 | B1 | 7/2014 | Lichtblau |
| 8,859,994 | B2 | 10/2014 | Deal |
| 9,522,201 | B2 | 12/2016 | Sunkara et al. |
| 10,556,025 | B2 | 2/2020 | Ufkes |
| 10,583,212 | B2 | 3/2020 | Ufkes |
| 10,639,390 | B2 | 5/2020 | Lloyd |
| 2007/0194717 | A1 | 8/2007 | Belikov |
| 2007/0208395 | A1* | 9/2007 | Leclerc .......... A61N 5/0616 607/86 |
| 2015/0025300 | A1 | 1/2015 | Hill et al. |
| 2019/0038914 | A1* | 2/2019 | Igarashi .......... G02B 5/28 |

FOREIGN PATENT DOCUMENTS

| | | |
|---|---|---|
| JP | 2002000706 | 1/2002 |
| JP | 3530954 | 5/2004 |
| KR | 100787874 | 12/2007 |
| RU | 2663459 | 8/2018 |
| WO | 2015030840 | 3/2015 |

OTHER PUBLICATIONS

English translation of KR100787874 abstract retrieved on Jun. 4, 2021 from "https://worldwide.espacenet.com/patent/search/family/039147747/publication/KR100787874B1?q=pn%3DKR100787874B1".

English translation of JP3530954 abstract retrieved on Jun. 4, 2021 from "https://worldwide.espacenet.com/patent/search/family/026394502/publication/JP3530954B2?q=pn%3DJP3530954B2".

English translation of JP2002000706 abstract retrieved on Jun. 4, 2021 from "https://worldwide.espacenet.com/?patent/search/family/018684815/publication/JP2002000706A?q=pn%3DJP2002000706A".

English machine translation of CN105377312 abstract retrieved on Jun. 4, 2021 from "https://translationportal.epo.org/emtp/translate/?ACTION=abstract-retrieval&COUNTRY=CN&ENGINE=google&FORMAT=docdb&KIND=B&LOCALE=en_EP&NUMBER=105377312&SRCLANG=zh&TRGLANG=en".

* cited by examiner

DECONTAMINATION OF BODY SURFACES AND ARTICLES WITH HARMLESS RADIATION AND RELATED METHODS

This is a non-provisional claiming priority to U.S. Provisional Patent Application No. 63/032,472, filed May 29, 2020, which is incorporated by reference in its entirety.

FIELD OF THE INVENTION

The present invention relates generally to a system for disinfecting surfaces using particular electromagnetic and acoustic waves effective to degrade microbes. More particularly, the present invention relates to systems and methods for irradiating the exterior of a person's body and/or articles, such as clothing and shoes, to disinfect without harming human tissues.

DISCUSSION OF THE BACKGROUND

In light of recent pandemics and the ease with which contagious diseases can be transmitted between individuals in dense social settings of the modern world, a system is needed that is effective to quickly eliminate contagious microbes (e.g., bacteria and viruses) from people, clothing, shoes, and other surfaces without slowing social processes. Gathering places such as restaurants, movie theaters, malls, schools, public buildings, airports, transportation stations, and sports stadiums are opportunistic environments for the spread of contagious disease, and steps need to be taken to reduce the spread of disease in these spaces so that we can better deal with the challenges posed by contagious and life-threatening diseases.

Although there are existing electromagnetic sanitation systems capable of sanitizing small items, surfaces, and even entire individuals, they all share a fair number of drawbacks. For example, existing systems tend to utilize electromagnetic radiation that's considered harmful for human or animal tissue, and thus are only used for inanimate objects such as lab equipment or smartphones. Other systems that are intended for human usages may harm human tissue and thus limit radiation exposure to human tissue or avoid it altogether. As a result, these systems are not designed to encompass an entire individual in radiation for swift and thorough sanitation, since such a system would be hazardous to the individual. Thus, there remains a need for system operable of utilizing electromagnetic radiation to quickly sanitize all surfaces of an individual without harming the individual.

SUMMARY OF THE PRESENT INVENTION

The presently disclosed system and methods includes using biophotonic and/or phononic systems for deactivating viruses, bacteria, and other pathogens that may be present on people, their clothing, or other surfaces. Biophotonic refers to the use of photons in specific wavelengths of the FAR-Ultraviolet C radiation and/or FAR-Infrared C radiation to affect the interior structure and chemistry of bacteria and viruses to degrade them and render them harmless. The infrared radiation may also provide a phononic effect that degrades the physical conditions of the cell or virus sufficiently to disrupt the cellular machinery, deactivating the virus. Furthermore, a higher temperature Inside the UVIR system makes negligible the rate of propagation of the Virus. The system of the present invention is operable to use electromagnetic radiation to disinfect the exterior surfaces of living mammal animals without harming the animal's tissue, but still effective to degrade microbe and sanitize the exterior surfaces.

UV radiation is a spectrum of wavelengths of light (10 nm to 400 nm), much of which is effective to degrade microbes, but that can also be harmful to human and animal tissues. Some UV wavelengths (e.g., UVA) can cause skin damage, premature aging, skin cancer, eye damage and suppression of the immune system. It has been discovered that there are UV wavelengths that are both effective to degrade bacteria and viruses, but do not harm exterior tissues of human beings. Far UV-C wavelengths in the range of about 180 nm to about 230 nm have been found to have sufficient energy to penetrate both viruses and bacteria to damage the nucleic acids, proteins, and other important molecules, but to lack sufficient energy to penetrate the upper keratinized layer of squamous cells of human skin or eyes. Thus, these wavelengths cannot damage the underlying skin cells of the epidermis or the underlying tissues. The present invention utilizes these useful Far UV-C wavelengths in a system that is operable to disinfect skin surfaces, clothing, and other potentially contaminated surfaces in a quick and effective manner, thereby providing a practical solution for decontaminating people, their clothing and personal articles that does not waylay or cause intolerable inconvenience. Thus, the present inventions use radiation that is operable to degrade microbes without harming human and animal tissue.

In some embodiments, the present invention utilizes Far UV-C irradiation in the range of wavelengths of about 175 nm to about 230 nm (e.g., about 210 nm to about 230 nm, about 215 nm to about 225 nm, about 220 nm to about 225 nm, about 222 nm, or any value or range of values therein), optionally in combination with infrared radiation of particular wavelengths which is also assistive in degrading microbes. Far UV-C radiation in this range may not penetrate human skin beyond the dead, keratinized layers, and therefore does not pose any exposure threat to a person. However, because viral envelopes, bacterial cell walls, and other microbial barriers do not have sufficient thickness to prevent the passage of Far UV-C radiation in the range of wavelengths mentioned above. The UV radiation has sufficient energy to penetrate viruses and bacterial cells where it can strike and degrade organic molecules, such as DNA, RNA, Proteins, and other critical structural and functional molecules therein. The energy of the Far UV-C wavelengths in the above-mentioned range are sufficient to break C—C bonds, C—H bonds, and O—H bonds in such molecules, resulting in the degradation and inactivation thereof.

The infrared wavelengths that may be used as part of the present invention are in the range of about 3 μm to about 1 mm. Water absorbs infrared radiation in this range of Far IR-C wavelengths, and thus irradiation of microbes with such IR wavelengths can cause vibrational movement of water molecules within a bacterium or virus, resulting in rapid elevation of its internal temperature. Intracellular and intraviral water is highly ordered and dynamic, and its arrangement is critical to the internal function of the bacterium or virus. The Far IR-C radiation of the present invention may cause phononic excitation, resulting in vibrational disruption of the internal arrangement and infrastructure of the cell or virus. Such disruption of that ordered arrangement due to increased vibration caused by Far-IR-C radiation can disrupt the cellular machinery and internal function of a bacterium or virus. Additionally, the increase in temperature can cause changes in intracellular or intraviral pH, osmosis, and other internal conditions that damage the microbe.

In the present invention, a combination of the UV radiation and IR radiation discussed above are used together to sanitize surface tissues of a person, clothing and accessories worn by the person, and the surface of any other objects. These Far-UV-C and Far-IR-C radiation may be applied through one or more lamps placed in a sanitizing area, wherein an entire person and/or associated objects may be encompassed by radiation for a period sufficient to degrade all or nearly all of the microbes present on the person and/or objects to the point of eliminating the infectiousness thereof. This sanitizing area may be a specially designed irradiation station in which specialized Far UV-C and Far IR-C lamps are installed in a pre-determined and ordered manner that can be effectively used to degrade the microbes with prolonged exposure.

The irradiation station may be a specialized frame or opening with radiation lamps/emitters installed on the bottom, top and sides of the frame. For example, the floor of the frame may include grating or a window to allow for the radiation to decontaminate the underside of an in individual, while the emitters on the sidewalls and ceiling decontaminate the rest of the surface areas. The irradiation station may further comprise a controller that automatically initiates a timer when someone enters the station to ensure the individual knows when it's appropriate to leave the station. The irradiation station may further comprise an image acquisition device or a pressure sensor on the floor to determine whether an individual is ready to use the station. For more thorough and rapid sanitization of one or more individuals, a series of irradiation stations may be arranged to optimize the sanitation and flow of traffic into a desired area. In such examples, each irradiation station may be identical and contain a set of UV-C emitters, IR-C emitters, and a controller with associated sensor. In other examples, a single controller may operate all irradiation stations and each irradiation station may be specialized such that the emitters present within each station, the intensity at which radiation is emitted, and the sanitation time, may vary from station to station. In another example, the system may comprise a singular master irradiation station that is essentially a specialized sanitation room or tunnel (e.g., a decontamination space), with UV-C and IR-C emitters placed in a pre-determined and ordered manner that can be effectively used to degrade the microbes. In yet another example, the sanitation room may simply comprise a series of irradiation stations within the room, as well as supplemental UV-C and IR-C emitters.

This versatility of this system, as a single irradiation station, a series of irradiation stations, or a sanitation room enable it to be placed at the entrance and exit of any public space, such as hospitals, clinics, banks, supermarkets, pharmacies, stadiums, government buildings, malls, schools, universities, churches, massive transportation facilities such as airports, metro, rail, ships, airplane entrances, bus stations, and only requires easy access to electrical current. The sanitation or tunnel may also be portable so that it may be easily transported by a vehicle and used in a temporary setting, such as tented outdoor events or other situations where the need to control disease transmission is temporary.

In some examples, the sanitation room or tunnel may have a size that allows for a person to be within about 1 meter of a Far UV-C lamp or emitter for each surface of the person's body, clothing, and accessories. Multiple arrangements of assembly of the Far UV-C lamps inside the sanitation room are possible according to the specifications on power and irradiance of sourced Far-UV-C Lamps. For example, the room or tunnel may be designed for the passage of a single person or a single-file line of people therethrough with proximity to the UV lamp or emitter of about 1 meter. In such examples, the width of the room or tunnel may be about 2 meters to about 3 meter in width, and about 2 meters to about 3 meters in height, such that UV lamps or emitters placed on the interior sidewalls and ceiling of the sanitation room or tunnel are in sufficient proximity to the person or persons passing through to degrade microbes on the person or persons. The sanitation room may also include a grating in the floor with Far UV-C lamps or emitters present below the grating to allow Far UV-C radiation to be directed at the bottom of a person's footwear, feet, or other object placed on the floor of the sanitation room or tunnel. The sanitation room or tunnel may also include Far IR-C lamps or emitters interspersed with the UV lamps or emitters to simultaneously cause the phononic and other sanitizing effects discussed above.

In such examples, the sanitation room or tunnel has automatic doors at the entrance and exit points, may have multiple irradiation stations therein, where each person passing therethrough may be positioned. The room or tunnel may be arranged such that it is designed to accept multiple individuals at once, each person advancing to the next station therein in sequence. In such examples, each person may be treated multiple times while not spending too much time at any given station to keep people moving through the room or tunnel at a reasonable pace, avoid irritation of having to stand under relatively warm conditions for an extended period, and still expose the person to an effective amount of Far-UV-C and Far-IR-C irradiation. In such examples there may be 2 to 10 stations, and the person may be instructed by a cueing mechanism to remain in a station for a pre-determined period of about 10 seconds to about 45 seconds (e.g., about 15 seconds to about 30 seconds, or any period therein). Each station may have Far-UV-C lamps or emitters on both sidewalls, the ceiling, and under the grate in an alignment along a vertical plane. There may be additional lamps Far-UV-C and/or Far-IR-C emitters positioned at the front and/or back of the person that are aimed at the frontal and caudal aspects of the person.

In some examples, the controller may have an automated guidance system in communication with cueing mechanisms. The cueing mechanisms may be strategically placed throughout the sanitation room, such as in between each set of UV-C or IR emitters, or at each irradiation station to enable the controller to provide automated guidance. The cueing mechanisms may also be a sound system operable to play prerecorded messages or sound effects with one or more speakers. The prerecorded messages may be simple directions such as whether an individual may proceed into the sanitation room or an irradiation station, the proper stance or form for sanitation, or the duration of which an individual should remain in an area. The cueing mechanisms may also be an indicator light system based on intensity, correlated color temperature, and/or pulse width modulation. For example, indicator lights may follow a standard traffic light scheme, wherein a green light indicates that in individual should proceed, a red light indicates that the individual should wait and continue to be irradiated, and a yellow light indicates that the irradiation process is almost complete. Spotlighting and/or underlighting of the sanitation station may also be present to illuminate the sanitation station position to the individual to be sanitized. The controller may also be operable to control the radiation lamps and the entrance(s) and exit(s) of a sanitation room via automated doors, allowing them to function as cueing mechanisms. For example, the automatic entrance door may open automatically to indicate that room is ready to accept another occupant.

The controller may also be in communication with one or more image acquisition devices to detect individuals within or near the sanitation room or stations. The image acquisition devices may be infrared sensors or cameras with facial recognition capabilities. The image acquisition devices may be strategically placed to monitor incoming traffic, outgoing traffic, and intermediate traffic. For example, there may be an image acquisition device at the entrance and exit of the sanitation room and multiple image acquisition devices equally spaced on the walls within the sanitation room to ensure all areas are covered. The controller may also use the image acquisition device data to track one or more individuals' position or progress through the sanitation room or stations and guide them accordingly. For example, the controller may use image acquisition data to determine that an individual is moving through the sanitation room or irradiation stations too quickly for proper sanitation, or against cueing mechanisms/automated guidance. The controller may also use image acquisition data to approximate the surface area of an individual and associated items and estimate the length of time the individual should remain within the sanitation room or at a particular irradiation station. For example, it may be estimated that an individual with a relatively large surface area to sanitize, such as a customer with a child stroller, would require more time than a standard person. Although image acquisition devices may be the most practical for the current examples, it should be understood that in other embodiments, a human sensor, such as acoustic sensors and pressure-sensitive floor tiles or grates, may be operable to perform the same function and may include infrastructure and circuitry to support the function as in the preferred embodiment. In one example, floor pressure sensors may be located below a grate at the sanitation station, where the grate provides an approximate outline of the sanitation on which the person is directed to stand (e.g., a grate that is two feet by three feet wide, allowing enough space for the individual to stand with their feet spaced 24 inches apart).

In some examples, the automated guidance system provided by the controller may simply be time based, wherein the appropriate cueing mechanisms are activated at predetermined times. In other examples, the automated guidance may be based on a safety analysis performed by the controller to determine when the proper cue mechanism should be activated. The safety analysis may include tracking the distances between individuals in sanitation room or between stations via image acquisition devices to ensure all individuals maintain a certain distance (e.g., 6 feet apart). The safety analysis may also include how recently the sanitation room or irradiation station was occupied, to ensure the area has had sufficient time to be sanitized before permitting another individual. The safety analysis may also include utilizing image acquisition devices to identify probable pathogenic risks (e.g., sick people) based on their body temperatures. The safety analysis may further include whether the sanitation room or series of irradiation stations are approaching a max capacity. The max capacity may be a predetermined number of individuals or vary based on the individuals entering. For example, standard maximum capacity can be three individuals at once, an individual that is considered a pathogenic risk, or two groups of two individuals. The controller may also have a self-diagnostic function operable of determining if one or more radiation emitters, cueing mechanisms, image acquisition devices, or automatic doors are malfunctioning and may incorporate this information into the safety analysis.

In some examples, the safety analysis may also trigger a safety breach protocol wherein the controller detects a hazard, such as one or more individuals not following cues provided by the automated guidance system. For example, if one or more individuals ignore automated guidance cues and attempts to rush through the sanitation room, the safety analysis may trigger the safety breach protocol. The safety breach protocol may comprise completely sealing the exit of the sanitation room and utilizing cueing mechanisms to instruct all individuals within the sanitation room to exit the room to end safety breach protocol or resume normal functionality. For example, the sound system may play an alarm noise and/or a prerecorded message instructing all individuals to please exit the sanitation room and notify nearby personnel if desired. The safety breach protocol may comprise sealing the exit and instructing all individuals return or remain in the area they were at when the protocol was triggered to resume normal functionality. The safety breach protocol may notify nearby personnel via cueing mechanisms or remote personnel via electronic communication, such as on a telephone or computer network, that a safety breach has occurred.

It is to be understood that variations, modifications, and permutations of embodiments of the present invention, and uses thereof, may be made without departing from the scope of the invention. It is also to be understood that the present invention is not limited by the specific embodiments, descriptions, or illustrations or combinations of either components or steps disclosed herein. The embodiments were chosen and described in order to best explain the principles of the invention and its practical application, to thereby enable others skilled in the art to best utilize the invention and various embodiments with various modifications as are suited to the particular use contemplated. Although reference has been made to the accompanying figures, it is to be appreciated that these figures are exemplary and are not meant to limit the scope of the invention. It is intended that the scope of the invention be defined by the claims appended hereto and their equivalents.

It is an object of the present invention to provide a system that decreases the infection rates and propagation of novel corona virus and other infectious microbes.

It is a further object of the present invention to provide a decontamination system that allows for social and economic activity under the threat of contagious disease in a safer manner.

It is a further object of the present invention to provide a system that allows large gatherings of people while decreasing the risk of invention and the infection rate at such gatherings.

It is a further object of the present invention to provide a sanitizing system that can be safely used on humans and animals.

It is a further object of the present invention to provide a sanitizing system that is easy, safe, and quick to use, without the need for burdensome protocols and equipment, or significant human intervention.

The above-described objects, advantages and features of the invention, together with the organization and manner of operation thereof.

It is the further object of the present invention, to be a portable sanitation room, to be placed in any public location, with the purpose of decreasing the risk of CoV-19 and other viral infections.

DETAILED DESCRIPTION OF THE DRAWINGS

Figure 1:
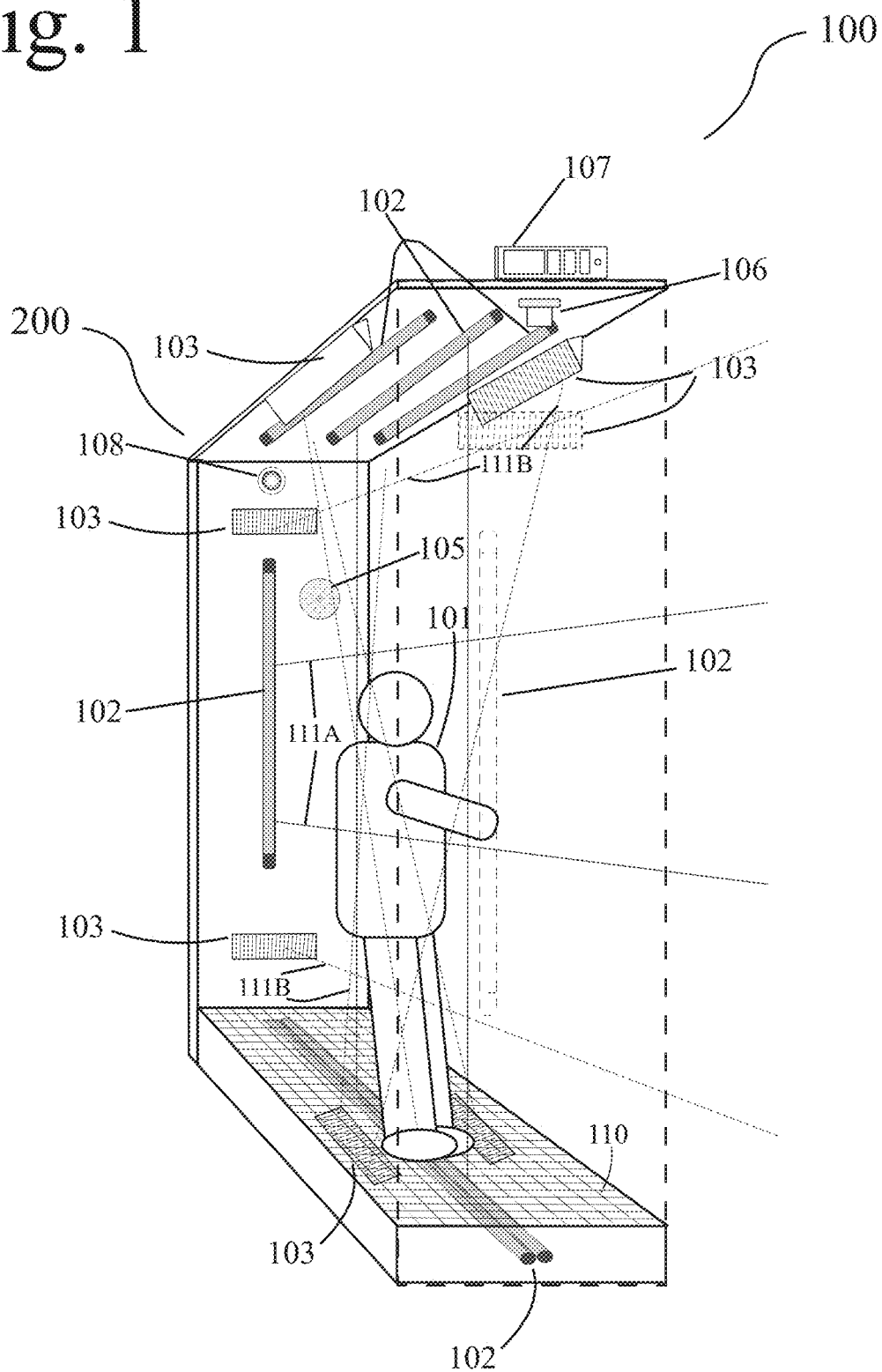
FIG. 1 shows an interior view of a controlled irradiation station according to an embodiment of the present invention.

Reference will now be made in detail to certain embodiments of the invention, examples of which are illustrated in the accompanying drawings. While the invention will be described in reference to these figures and certain implementations and examples of the embodiments, it will be understood that such implementations and examples are not intended to limit the invention. To the contrary, the invention is intended to cover alternatives, modifications, and equivalents that are included within the spirit and scope of the invention as defined by the claims. In the following disclosure, specific details are given to provide a thorough understanding of the invention. References to various features of the "present invention" throughout this document do not mean that all claimed embodiments or methods must include the referenced features. It will be apparent to one skilled in the art that the present invention may be practiced without these specific details or features.

Reference will be made to the exemplary illustrations in the accompanying drawings, and like reference characters may be used to designate like or corresponding parts throughout the several views of the drawings.

As shown in FIG. 1, the germicidal irradiation system 100 utilizes a combination of the UV radiation 111A and IR radiation 111B to sanitize surface tissues of a person 101, including clothing, accessories, and the surface of any other objects. These Far-UV-C and Far-IR-C radiation 111 may be applied through one or more lamps (102 and 103) placed in a sanitizing area, wherein an entire person and/or associated objects may be encompassed by radiation 111 for a period sufficient to degrade all or nearly all of the microbes present on the person and/or objects to the point of eliminating the infectiousness thereof. This sanitizing area may be a specially designed irradiation station 200 in which specialized Far UV-C and Far IR-C lamps 102 and 103 are installed in a pre-determined and ordered manner that can be effectively used to degrade the microbes 114 with prolonged exposure, as shown in FIG. 5.

The irradiation station 200 may be a specialized frame or opening with radiation lamps/emitters installed on all interior sides of the frame. For example, the floor of the frame may include grating 110 or a window to allow for the radiation to decontaminate the underside of an in individual 101, while the emitters 102 and 103 on the sidewalls and ceiling decontaminate the rest of the surface areas of the individual. The irradiation station 200 may further comprise a controller 107 that may automatically power on the lamps 102 and 103 and initiate a timer when someone enters the station to ensure the individual knows when it's appropriate to leave the station. The irradiation station may further comprise an image acquisition device 108 or pressure sensor to determine whether an individual is ready to use the station. For more thorough and rapid sanitization of one or more individuals, a series of irradiation stations 200 may be arranged to optimize the sanitation and flow of traffic into a desired area. In such examples, each irradiation station 200 may be identical and contain a set of UV-C emitters 102, IR-C emitters 103, and a controller 107 with associated sensors 108. In other examples, a single controller 107 may operate all irradiation stations 200 and each irradiation station may be specialized such that the emitters 102 and 103 present within each station, the intensity at which radiation 111 is emitted, and the sanitation time, may vary from station to station.

Figure 2:
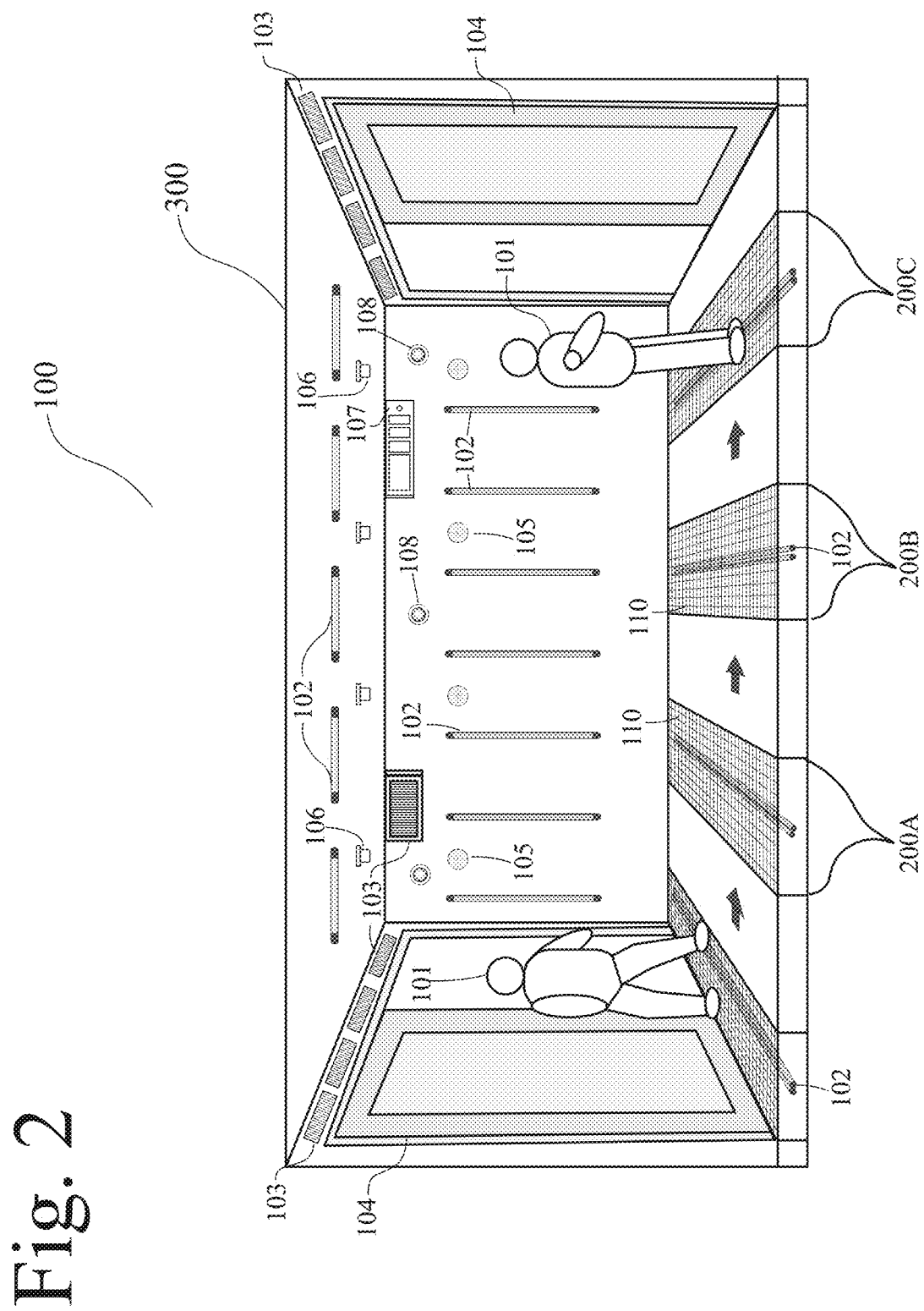
FIG. 2 shows an interior view of a controlled sanitation room according to an embodiment of the present invention.

In another example, as shown in FIG. 2, the system 100 may comprise a singular master irradiation station that is essentially a specialized sanitation room or tunnel 300 (e.g., a decontamination space), with UV-C and IR-C emitters 102 and 103 placed in a pre-determined and ordered manner that can be effectively used to degrade the microbes 114 over the entire surface of the individual. In yet another example, the sanitation room 300 may comprise a series of irradiation stations 200 within the room, as well as supplemental UV-C and IR-C emitters.

Figure 5:
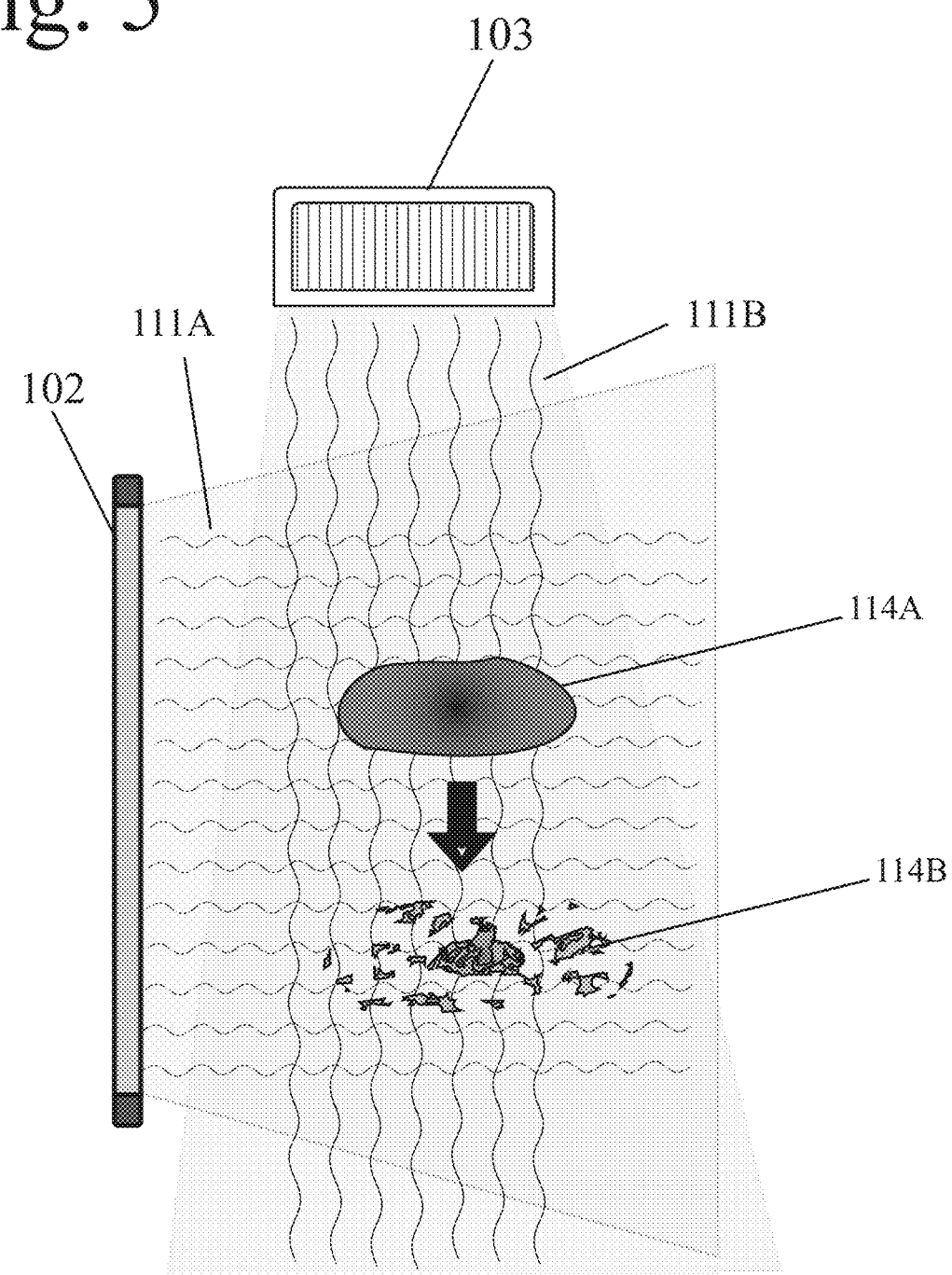
FIG. 5 shows a pathogen before and after exposure to irradiation by a controlled sanitation room or station according to an embodiment of the present invention.
Figure 6:
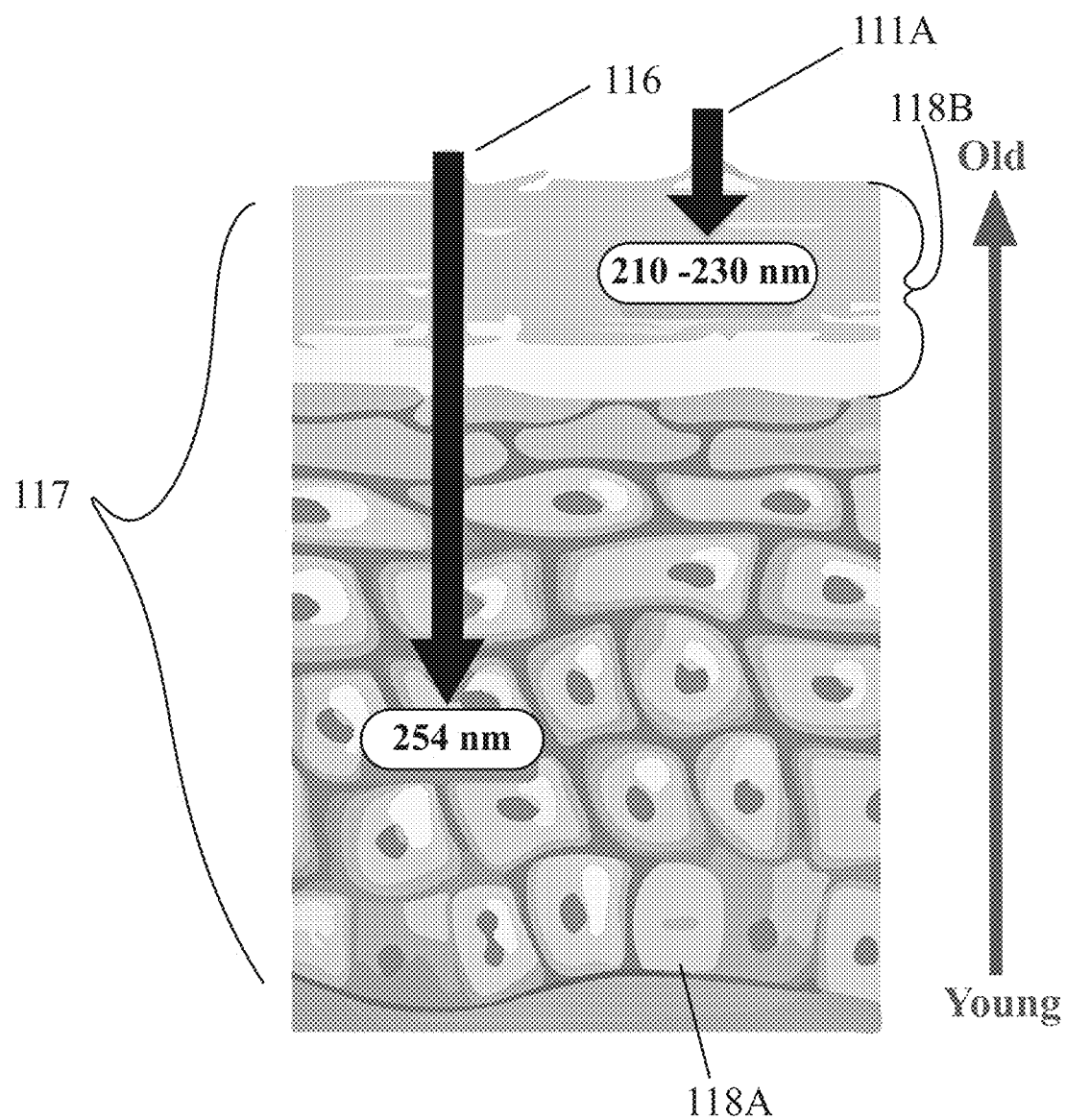
FIG. 6 shows skin penetration of UV irradiation at different wavelengths.

As shown in FIG. 5, the present invention utilizes Far UV-C irradiation 111A in the range of wavelengths of about 175 nm to about less than 230 nm (e.g., about 210 nm to about 230 nm, about 215 nm to about 225 nm, about 220 nm to about 225 nm, about 222 nm, or any value or range of values therein), optionally in combination with infrared radiation 111B of particular wavelengths which further accelerates the transition of microbes 114 from an active state 114A to a deactivated state 114B. As shown in FIG. 6, far UV-C radiation in this range may not penetrate human skin or epidermis 117 beyond the dead, keratinized layers 118B, and therefore does not pose any exposure threat to a person. However, because viral envelopes, bacterial cell walls, and other microbial barriers do not have sufficient thickness to prevent the passage of Far UV-C radiation 111A in the range of wavelengths mentioned above. The UV radiation 111A has sufficient energy to penetrate viruses and bacterial cells where it can strike and degrade organic molecules, such as DNA, RNA, Proteins, and other critical structural and functional molecules therein. The energy of the Far UV-C wavelengths in the above-mentioned range are sufficient to break C—C bonds, C—H bonds, and O—H bonds in such molecules, resulting in the degradation and inactivation thereof.

Figure 3:
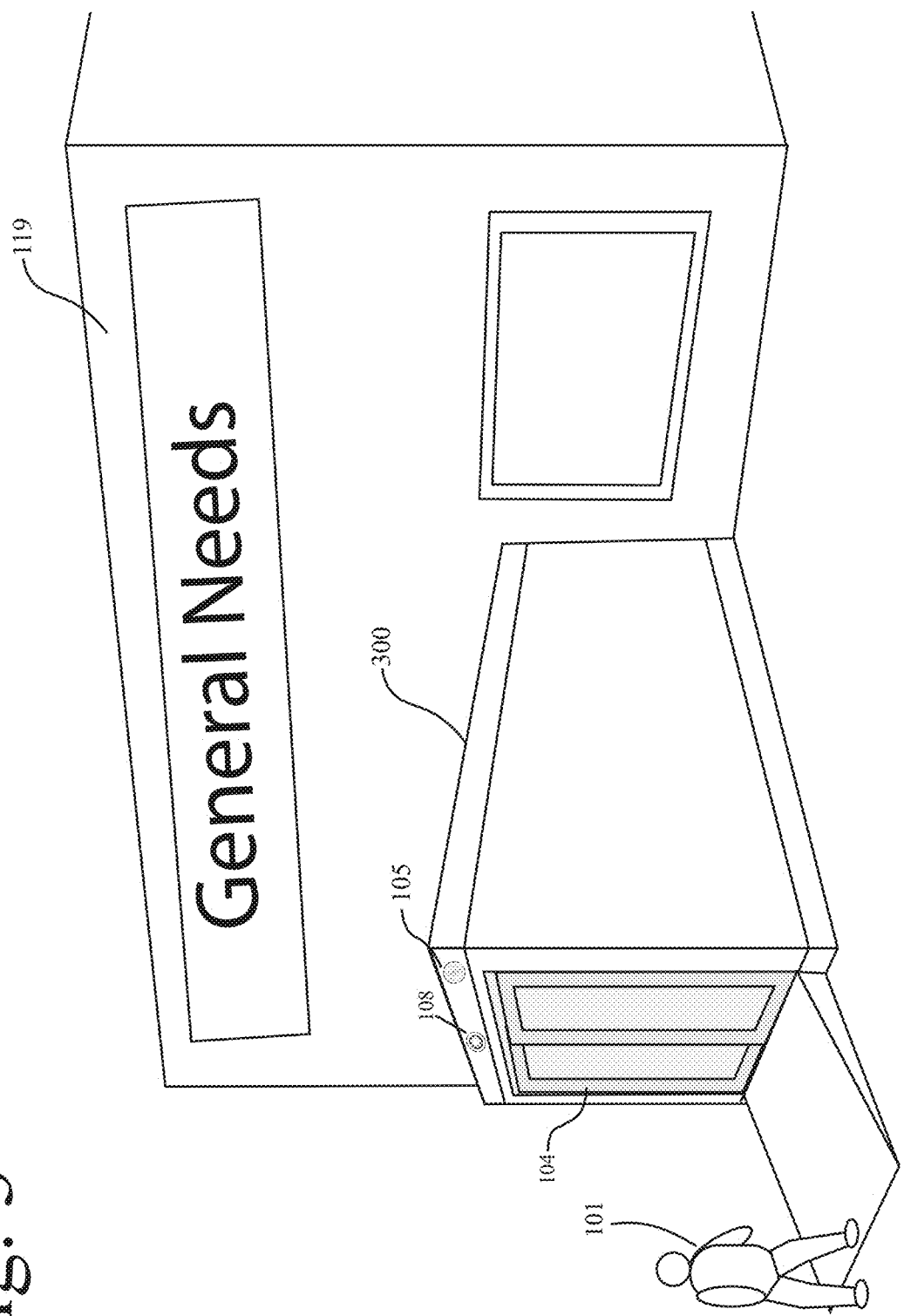
FIG. 3 shows an exterior perspective view of a controlled sanitation room in a practical setting according to an embodiment of the present invention.
Figure 4:
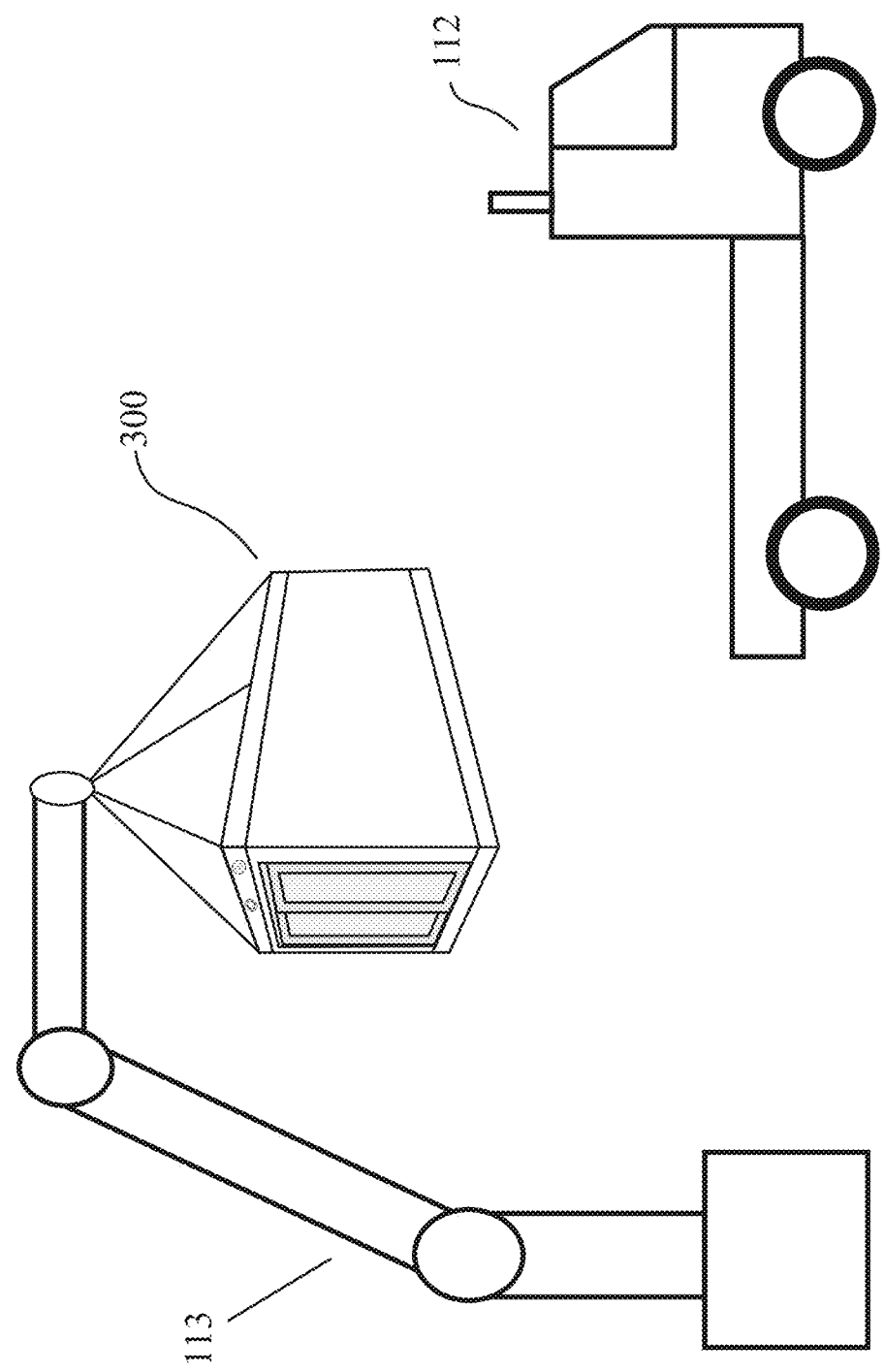
FIG. 4 shows the portability aspect of a controlled sanitation room according to an embodiment of the present invention.

As shown in FIG. 3, the versatility of this system 100, as a single irradiation station, a series of irradiation stations, or a sanitation room 300 enable it to be placed at the entrance and exit of any public space 119, such as hospitals, clinics, banks, supermarkets, pharmacies, stadiums, government buildings, malls, schools, universities, churches, massive transportation facilities such as airports, metro, rail, ships, airplane entrances, bus stations, and only requires easy access to electrical current. As shown in FIG. 4, the sanitation room 300 may also be portable so that it may be easily transported by a vehicle 112 and used in a temporary setting, such as tented outdoor events or other situations where the need to control disease transmission is temporary. While FIG. 4 shows the sanitation room 300 being mounted onto the vehicle 112 with a crane-like device 113. It should be understood that this can be done by other practical means.

In some examples, as shown in FIGS. 2-3, the irradiation station 200 or sanitation room 300 may have a size that allows for a person to be within about 1 meter of a Far UV-C lamp or emitter for each surface of the person's body, clothing, and accessories. Multiple arrangements of assembly of the Far UV-C 102 lamps inside the sanitation room 300 are possible according to the specifications on power and irradiance of sourced Far-UV-C Lamps 102. For example, the sanitation room 300 may be designed for the passage of a single person or a single-file line of people therethrough with proximity to the UV lamp or emitter of about 1 meter. In such examples, the width of the room or tunnel may be about 2 meters to about 3 meter in width, and about 2 meters to about 3 meters in height, such that UV lamps or emitters placed on the interior sidewalls and ceiling of the sanitation room or tunnel are in sufficient proximity to the person or persons passing through to degrade microbes on the person or persons. The sanitation room 300 may also include a grating or UV-translucent window 110 (e.g., quartz or other UV-translucent material) in the floor with Far UV-C lamps 102 or emitters present below the grating to allow Far UV-C radiation 111A to be directed at the bottom of a person's footwear, feet, or other object placed on the floor of the sanitation room 300. The sanitation room 300 may also include Far IR-C lamps or emitters 103 interspersed with the UV lamps or emitters to simultaneously cause the phononic and other sanitizing effects discussed above.

As shown in FIG. 2, the sanitation room 300 or tunnel may have automatic doors 104 at the entrance and exit points, may have multiple irradiation stations 200a, 200b, and 200c therein, where each person 101 passing therethrough may be positioned. The room or tunnel may be arranged such that it is designed to accept multiple persons at once, each person advancing to the next station therein in sequence. In such examples, each person may be treated multiple times for a pre-determined period at each station 200 to keep individuals 101 moving through the room or tunnel at a reasonable pace, avoid irritation of having to stand under relatively warm conditions for an extended period, and still expose the person 101 to an effective amount of Far-UV-C and Far-IR-C irradiation 111. In such examples there may be 2 to 10 stations 200, and the person may be instructed by a cueing mechanism, such as one or more indicator lights 105 and/or one or more annunciators 106, for a period of about 10 seconds to about 45 seconds. The pre-determined period for one or more of the stations may be different than the others (e.g., station 200a may include a 45 sec. radiation period, the station 200b may have a 30 sec. irradiation period, and the station 200c may having a 20 sec. irradiation period), and the irradiation intensity of the lamps 102 and 103 one or more of the stations may be different than the others. For example, each UV-C lamp 102 may have a different Far-UV-C irradiation output in a range of 100 mW Far-UV-C to about one Watt Far-UV-C, and each station may have a different Far-IR-C irradiation output in a range of 100 mW Far-IR-C to about one Watt Far-IR-C. Each station may have Far-UV-C lamps or emitters 102 on both sidewalls, the ceiling, and under the grate in an alignment along a vertical plane. There may be additional lamps Far-UV-C and/or Far-IR-C emitters 102 and 103 positioned at the front and/or back of the person that are aimed at the frontal and caudal aspects of the person.

In some examples, the controller 107 may have an automated guidance system in communication with cueing mechanisms. The cueing mechanisms may be strategically placed throughout the sanitation room 300, such as in between each set of UV-C or IR emitters, or at each irradiation station 200 to enable the controller 107 to provide automated guidance. The cueing mechanisms may also be a sound system operable to play prerecorded messages and/or sound effects with one or more speakers 105. The prerecorded messages may be simple directions such as whether an individual may proceed into the sanitation room or an irradiation station, the proper stance or form for sanitation, or the duration of which an individual should remain in an area. The cueing mechanisms may also be an indicator light system based on intensity, correlated color temperature, and/or pulse width modulation. For example, indicator lights 106 may follow a standard traffic light color scheme, wherein a green light indicates that in individual should proceed, a red light indicates that the individual should wait and continue to be irradiated, and a yellow light indicates that the irradiation process is almost complete. The controller 107 may also be operable to control the radiation lamps 102 and 103 and the entrance(s) and exit(s) of a sanitation room 100 via automated doors 104, allowing them to function as cueing mechanisms. For example, the automatic entrance door 104 may open automatically to indicate that room is ready to accept another occupant.

The controller 107 may also be in communication with one or more image acquisition devices 108 to detect individuals 101 within or near the sanitation room 300 or stations 200. The optical sensor devices 108 may be infrared image sensors and/or cameras with facial recognition capabilities. The optical sensor devices 108 may be strategically placed to monitor incoming traffic, outgoing traffic, and intermediate traffic. For example, there may be an optical sensor device 108 at the entrance and exit of the sanitation room 300 and multiple optical sensor devices 108 equally spaced on the walls within the sanitation room 300 to ensure all areas are covered. The controller may also use the optical sensor device data to track one or more individuals' position or progress through the sanitation room 300 or stations 200 and guide them accordingly. For example, the controller 107 may use optical sensor device data to determine that an individual is moving through the sanitation room 300 or irradiation stations 200 too quickly for proper sanitation, or against cueing mechanisms/automated guidance. The controller 107 may also use optical sensor device data to approximate the surface area of an individual 101 and associated items and estimate the length of time the individual should remain within the sanitation room 300 or at a particular irradiation station 200. For example, it may be estimated that an individual with a relatively large surface area to sanitize, such as a customer with a child stroller, would require more time than a standard person. Although optical sensor devices 108 may be the most practical for the current examples, it should be understood that in other embodiments acoustic sensors, pressure-sensitive floor tiles, and/or other sensor devices in electronic communication with the controller 107 may be used in addition to or alternatively to the optical sensors, and may be operable to monitor the position and advancement of people passing through the sanitation system 100.

In some examples, the automated guidance system provided by the controller 107 may simply be time based, wherein the appropriate cueing mechanisms 105 and/or 106 are activated at predetermined times. In other examples, the automated guidance may be based on a safety analysis performed by the controller 107 to determine when the proper cue mechanism should be activated. The safety analysis may include tracking the distances between individuals in sanitation room 300 or between stations 200 via optical sensor devices 108 to ensure all individuals maintain a certain distance (e.g., 6 feet apart). The safety analysis may also include how recently the sanitation room 300 or irradiation station 200 was occupied, to ensure the area has had sufficient time to be sanitized before permitting another individual. The safety analysis may also include utilizing optical sensor devices 108 to identify probable pathogenic risks (e.g., sick people) based on their body temperatures. The safety analysis may further include whether the sanitation room 300 or series of irradiation stations 200 are approaching a max capacity. The max capacity may be a predetermined number of individuals or vary based on the individuals entering. For example, standard maximum capacity can be three individuals at once, an individual that is considered a pathogenic risk, or two groups of two individuals. The controller 107 may also have a self-diagnostic function operable of determining if one or more radiation emitters 102 and 103, cueing mechanisms 105 and 106, optical sensor devices 108, or automatic doors 104 are malfunctioning and may incorporate this information into the safety analysis.

In some examples, the safety analysis may also trigger a safety breach protocol wherein the controller 107 detects a hazard, such as an individual not following cues provided by the automated guidance system or malfunctioning equipment. For example, if one or more individuals ignore automated guidance cues and attempts to rush through the sanitation room 300, the safety analysis may trigger the safety breach protocol. The safety breach protocol may comprise completely sealing the exit of the sanitation room 300 and utilizing cueing mechanisms to instruct all individuals within the sanitation room 300 to exit the room to end safety breach protocol or resume normal functionality. For example, the annunciators 106 may play an alarm noise and/or a prerecorded message instructing all individuals to please exit the sanitation room 300 and notify nearby personnel if desired. The safety breach protocol may comprise sealing the exit and instructing all individuals return or remain in the area they were at when the protocol was triggered to resume normal functionality. The safety breach protocol may notify nearby personnel via cueing mechanisms 105 and 106 or remote personnel via electronic communication, such as a Wi-Fi or a cellular network, that a safety breach has occurred.

It is to be understood that variations, modifications, and permutations of embodiments of the present invention, and uses thereof, may be made without departing from the scope of the invention. It is also to be understood that the present invention is not limited by the specific embodiments, descriptions, or illustrations or combinations of either components or steps disclosed herein. The embodiments were chosen and described in order to best explain the principles of the invention and its practical application, to thereby enable others skilled in the art to best utilize the invention and various embodiments with various modifications as are suited to the particular use contemplated. Although reference has been made to the accompanying figures, it is to be appreciated that these figures are exemplary and are not meant to limit the scope of the invention. It is intended that the scope of the invention be defined by the claims appended hereto and their equivalents.

What is claimed:

1. A germicidal irradiation system comprising a decontamination space wherein:
   a. at least one UV radiation emitter plurality of electromagnetic radiation emitters in a first predetermined position operable to emit radiation in a predetermined range of UV wavelengths that does not penetrate beyond the stratum corneum of the skin;
   b. at least one IR radiation emitter in a second predetermined position operable to emit IR radiation in a predetermined range of IR wavelengths, wherein exposure of human or animal tissue to said UV radiation and said IR radiation for a pre-determined period is operable to deactivate or kill pathogens without harming said human or animal tissue; and
   c. an automated guidance system that includes at least one cueing mechanism utilized to guide said human subject through said decontamination space.

2. The system of claim 1, wherein said predetermined range of UV wavelengths is from about 170 nm to about 230 nm.

3. The system of claim 1, wherein said predetermined range of IR wavelengths is from about 3 μm to about 1 mm.

4. The system of claim 1, wherein said decontamination space is an enclosed space operable to safely accommodate a human subject.

5. The system of claim 4, wherein said decontamination space further comprises a controller in communication with said automated guidance system.

6. The system of claim 5, wherein said at least one cueing mechanisms include at least one of the following:
   a. a sound-producing device comprising of at least one speaker,
   b. a light-producing device comprising at least one indicator light, and
   c. automatic doors operable of halting passage through said decontamination space.

7. The system of claim 6, wherein said controller is operable to perform a safety analysis based on electronic data provided by said automated guidance system, wherein said controller further comprises a safety breach protocol triggered when safety analysis detects a malfunction of said at least one UV radiation emitter, said at least one IR radiation emitter, said at least one image device, or at least one automatic door.

8. The system of claim 4, wherein said decontamination space further comprises a series of irradiation stations each encompassing a plurality of UV radiation emitters arranged in a first pattern that irradiates all surface areas of said subject when present in said irradiation station.

9. The system of claim 4, wherein each of said series of irradiation stations encompasses a plurality of IR radiation emitters arranged in a second pattern that irradiates all surface areas of said subject when present in said irradiation station.

10. The system of claim 1, wherein a first predetermined range from said at least one predetermined range comprises wavelengths between 210 nm to 230 nm.

11. The system of claim 1, wherein the first predetermined range from said at least one predetermined range comprises wavelengths at 222 nm.

12. A germicidal irradiation system comprising a series of irradiation station comprising:
   a series of irradiation stations each having cueing mechanisms utilized to guide at least one subject through said series of irradiation stations; and
   a plurality of electromagnetic radiation emitters arranged in predetermined locations in each of said irradiation stations to optimally irradiate said at least one subject in a first predetermined range of UV wavelengths and a second predetermined range of IR wavelengths, wherein exposure to said first predetermined range and said second predetermined range deactivates or kills pathogens without harming human or animal tissue.

13. The system of claim 12, wherein said first predetermined range comprises wavelengths between 170 nm to 230 nm.

14. The system of claim 13, further comprising at least one controller with an automated guidance system in communication with said cueing mechanisms.

15. The system of claim 12, wherein said second predetermined range comprises wavelengths within 3 µm to 1 mm.

16. A method for utilizing electromagnetic radiation to deactivate or kill pathogens on the surface of a subject without harming human or animal tissue, comprising:
  guiding at least one subject through a plurality of irradiation stations in a series, each having electromagnetic radiation emitters therein;
  exposing said human or animal tissue to a first range of electromagnetic radiation emitter in the UV spectrum, and a second range of electromagnetic radiation in the IR spectrum, wherein a controller is used to control said electromagnetic radiation emitters of each irradiation station.

17. The method of claim 16, wherein said first range of electromagnetic radiation comprises wavelengths from 170 nm and 230 nm.

18. The method of claim 16, wherein said second range of electromagnetic radiation comprises wavelengths from 3 µm to 1 mm.

19. The method of claim 16, wherein said controller is operable of detecting an incoming said subject and provide automated guidance to said subject via cueing mechanisms.

* * * * *